(12) United States Patent
Xie et al.

(10) Patent No.: US 11,717,008 B2
(45) Date of Patent: Aug. 8, 2023

(54) PROBIOTIC FERMENTED FRUIT AND VEGETABLE PULP COMPOSITION CONTAINING ACTIVE BACTERIA AND PREPARATION METHOD THEREOF

(71) Applicant: Nanchang University, Nanchang (CN)

(72) Inventors: Mingyong Xie, Nanchang (CN); Tao Xiong, Nanchang (CN); Qianqian Guan, Nanchang (CN)

(73) Assignee: NANCHANG UNIVERSITY, Jiangxi (CN)

( * ) Notice: Subject to any disclaimer, the term of this patent is extended or adjusted under 35 U.S.C. 154(b) by 299 days.

(21) Appl. No.: 17/035,811

(22) Filed: Sep. 29, 2020

(65) Prior Publication Data

US 2021/0106029 A1    Apr. 15, 2021

Related U.S. Application Data

(63) Continuation-in-part of application No. 16/833,642, filed on Mar. 29, 2020.

(30) Foreign Application Priority Data

Feb. 18, 2020    (CN) .......................... 202010127835.9

(51) Int. Cl.
    *A23L 2/38*        (2021.01)
    *A23L 2/04*        (2006.01)
    (Continued)

(52) U.S. Cl.
    CPC ................. *A23L 2/382* (2013.01); *A23L 2/04* (2013.01); *A23L 2/46* (2013.01); *A23L 2/60* (2013.01); *A23L 19/09* (2016.08); *A23L 33/125* (2016.08); *A23L 33/135* (2016.08); *A23L 33/15* (2016.08); *A23V 2002/00* (2013.01);
    (Continued)

(58) Field of Classification Search
    None
    See application file for complete search history.

(56) References Cited

PUBLICATIONS

Yurkow: Nomenclatural issues concerning cultured yeasts and other fungi: why it is important to avoid unneeded name changes; Yurkov et al. IMA Fungus (2021) 12:18; https://doi.org/10.1186/s43008-021-00067-x (Year: 2021).*

(Continued)

*Primary Examiner* — Patricia A George
(74) *Attorney, Agent, or Firm* — Michael Ye; Rimon Law

(57) ABSTRACT

The present invention belongs to the technical field of beverages, and relates to a probiotic fermented fruit and vegetable puree composition containing active bacteria and its preparation method. The composition containing active bacteria is obtained by fermenting fruit and vegetable puree with *Lactobacillus casei* NCU215. The probiotic fermented fruit and vegetable puree has the following characteristics: the probiotic fermented fruit and vegetable puree may generate a natural mellow sour, effectively remove an astringency in fruit and a wild *Artemisia* flavor in vegetable, and neutralize an unpleasant sour in the fruit; with probiotic fermentation, the present invention may improve a content of amino acid in the fruit and vegetable by 20% or more, generate multiple aromatic substances, improve a flavor substance by 30% or more, and effectively improve a taste and a mouthfeel of the product; the present invention prolongs a shelf life of the product and prevents rot.

1 Claim, 2 Drawing Sheets

Specification includes a Sequence Listing.

(51) Int. Cl.
  *A23L 2/60*     (2006.01)
  *A23L 33/135*   (2016.01)
  *A23L 33/15*    (2016.01)
  *A23L 2/46*     (2006.01)
  *A23L 19/00*    (2016.01)
  *A23L 33/125*   (2016.01)
  *A61K 35/747*   (2015.01)
  *A61K 47/46*    (2006.01)
  *A61K 47/22*    (2006.01)
  *A61K 47/26*    (2006.01)

(52) U.S. Cl.
  CPC ......... *A23Y 2220/17* (2013.01); *A61K 35/747* (2013.01); *A61K 47/22* (2013.01); *A61K 47/26* (2013.01); *A61K 47/46* (2013.01)

(56) References Cited

PUBLICATIONS

Nic: Important statistical concepts: significance, strength, association, causa and other statistical concepts; published online at least by Feb. 5, 2020 at https://web.archive.org/web/20200205034159/ https://creativemaths.net/blog/significance/ (Year: 2020).*

Link: The 13 Healthiest Root Vegetables, published online at least by Dec. 6, 2018 at: https://web.archive.org/web/20181206113212/ https://www.healthline.com/nutrition/root-vegetables#section9 (Year: 2018).*

Suying: CN 107080209 A; Publication Date: Aug. 22, 2017 (Year: 2017).*

* cited by examiner

SEQUENCE LISTING

```
<160> NUMBER OF SEQ ID NOS: 1

<210> SEQ ID NO 1
<211> LENGTH: 1194
<212> TYPE: DNA
<213> ORGANISM: Lactobacillus casei

<400> SEQUENCE: 1
cggcagtgcg ggtgctatac atgcaagtcg aacgagttct cgttgatgat cggtgcttgc      60
accgagattc aacatggaac gagtggcgga cgggtgagta acacgtgggt aacctgccct     120
taagtggggg ataacatttg gaaacagatg ctaataccgc atagatccaa gaaccgcatg     180
gttcttggct gaaagatggc gtaagctatc gcttttggat ggacccgcgg cgtattagct     240
agttggtgag gtaatggctc accaaggcga tgatacgtag ccgaactgag aggttgatcg     300
gccacattgg gactgagaca cggcccaaac tcctacggga ggcagcagta gggaatcttc     360
cacaatggac gcaagtctga tggagcaacg ccgcgtgagt gaagaaggct ttcgggtcgt     420
aaaactctgt tgttggagaa gaatggtcgg cagagtaact gttgccggcg tgacggtatc     480
caaccagaaa gccacggcta actacgtgcc agcagccgcg gtaatacgta ggtggcaagc     540
```

```
gttatccgga tttattgggc gtaaagcgag cgcaggcggt tttttaagtc tgatgtgaaa    600
gccctcggct taaccgagga agcgcatcgg aaactgggaa acttgagtgc agaagaggac    660
agtggaactc catgtgtagc ggtgaaatgc gtagatatat ggaagaacac cagtggcgaa    720
ggcggctgtc tggtctgtaa ctgacgctga ggctcgaaag catgggtagc gaacaggatt    780
agataccctg gtagtccatg ccgtaaacga tgaatgctag gtgttggagg gtttccgccc    840
ttcagtgccg cagctaacgc attaagcatt ccgcctgggg agtacgaccg caaaggttga    900
aactcaaagg aattgacggg ggcccgcaca agcggtggag catgtgggtt taattcgaag    960
caacgcgaag aacccttacc aggtcttgac atctttgat cacctgagag atcagttttc    1020 cccttcggg gcaaaatgac aggtggtgca tgatgtcgtc agcctcgtgt cgtgagatgg    1080
tggggtaggt cccgcacgag cgcacctatg aactagtgca gcattagttg gtcactctag    1140
tagactgcag tgacgaccgg aggcaacgtt ggaatgaacg gttcaattca tcag         1194
```

PROBIOTIC FERMENTED FRUIT AND VEGETABLE PULP COMPOSITION CONTAINING ACTIVE BACTERIA AND PREPARATION METHOD THEREOF

CROSS REFERENCE TO RELATED APPLICATION

This application is a Continuation-In-Part of U.S. Ser. No. 16/833,642 entitled "PROBIOTIC FERMENTED FRUIT AND VEGETABLE PULP PRODUCT", with a filing date of Mar. 29, 2020, now pending, which claims priority to Chinese application no. 2020101278359 filed on 2020 Feb. 18. The content of the aforementioned applications, including any intervening amendments thereto, are incorporated herein by reference.

REFERENCE TO AN ELECTRONIC SEQUENCE LISTING

The contents of the electronic sequence listing (Untitled ST25.txt; Size: 2,000 bytes; and Date of Creation: SEP 9, 2020) is herein incorporated by reference in its entirety.

FIELD OF TECHNOLOGY

The present invention belongs to the technical field of beverages, and in particular to a probiotic fermented fruit and vegetable puree product.

BACKGROUND

At present, main fruit and vegetable puree products on a market at home and abroad are pineapple puree, hawthorn puree, mango puree and apple puree, and the production process often includes the steps of cleaning, pulping (juicing), concentrating, blending, filling and sterilizing. For example, CN 105995710 A discloses a method for fermenting fruit and vegetable pulp by adopting plant probiotics. The method is completed by the steps of fruit and vegetable pretreatment, crushing, softening, fruit and vegetable pulping, blending, primary sterilization and cooling, fermentation, centrifugation, degassing, homogenization, secondary sterilization and cooling, and sterile filling. The method has the beneficial effects that the fruit and vegetable pulp with a weak acidity is fermented by different *Lactobacillus* to generate a large amount of organic acid such as lactic acid, thus reducing a pH of the fruit and vegetable pulp, generating a good fermentation flavor, reducing a sterilization condition, saving cost, retaining nutrition of fruit and vegetable, and increasing nutritional ingredients of the fermentation product; meanwhile, fermented fruit and vegetable puree is centrifuged by a horizontal spiral centrifuge to separate yeast mud, thus effectively improving the utilization stability of the fermented fruit and vegetable pulp in the beverage industry. The method solves the problems that low-acid and acidic fruit and vegetable puree has a shorter shelf life, the product flavor is not good, the processing cost is high and the nutrition loss is serious during processing. CN 107136372 A discloses a method for fermenting *Smallanthus sonchifolius* pulp by plant probiotics. The method is completed by the steps of pretreatment, crushing, softening, pulping, enzymolysis, blending, primary sterilization and cooling, fermentation, centrifugation, degassing, homogenization, secondary sterilization and cooling, and sterile filling. The method has the beneficial effects that the *Smallanthus sonchifolius* pulp with a weak acidity is fermented by different *Lactobacillus* to generate a large amount of organic acid such as lactic acid, thus reducing a pH of the *Smallanthus sonchifolius* pulp, generating a good fermentation flavor, reducing a sterilization condition, saving cost, retaining nutrition of the *Smallanthus sonchifolius*, and increasing nutritional ingredients of the fermentation product; meanwhile, fermented fruit and vegetable puree is centrifuged by a horizontal spiral centrifuge to separate yeast mud, thus effectively improving the stability of the fermented *Smallanthus sonchifolius* pulp, and expanding use of the *Smallanthus sonchifolius* in the beverage industry.

In the prior art, it is ordinary that the flavor in the product is mainly produced by blending with an essence. During production, due to a great loss of nutritional ingredients in fruit and vegetable raw materials, there are problems that the product has an uncoordinated fragrance and a complex production process, etc.

The present invention independently screens a probiotic strain having good fruit and vegetable fermentability to ferment fruit and vegetable puree, thus effectively keeping the nutritional ingredients in the fruit and vegetable raw materials; and by means of a fermentation process, the product keeps a main flavor, with more varieties of fragrances and more mellow puree. Without any essence, pigment and preservative, the product is a novel environment-friendly fermented fruit and vegetable puree product.

SUMMARY

An objective of the present invention is to provide novel probiotic fermented fruit and vegetable puree, which is obtained by taking fresh fruit and vegetable as raw materials and fermenting them via a probiotic, and has rich nutritional ingredients and a certain function. The probiotic fermented fruit and vegetable puree prepared with a method provided by the present invention fully keeps sarcocarp and juice in the fresh fruit and vegetable, implements maximized utilization of the raw materials, and has a good fermentation flavor of fruit and vegetable, a bright color, a mellow taste, a pleasant fragrance, and a certain acceleration effect to an intestinal function of a human body.

The probiotic fermented puree provided by the present invention is prepared by fermenting the following raw materials: 80-99.8 parts of fruit and vegetable puree, and 0-19.8 parts of syrup or sugar substitute.

Further, the raw materials further include 0.01-0.5 parts of D-sodium isoascorbiate or vitamin C.

Further, the syrup or the sugar substitute is white granulated sugar, glucose, starch syrup, malt syrup, glucose syrup, maltitol, xylitol, erythritol or isomaltooligosaccharide.

A method for producing the probiotic fermented fruit and vegetable puree by fermenting the above-mentioned raw materials is as follows:

(1) Selecting unrotten and fresh fruit and vegetable as raw materials, cleaning, removing an inedible portion, pulping or juicing to obtain fruit and vegetable puree, stirring uniformly according to the above components and proportion, and sterilizing.

Further, the fresh fruit and vegetable are precooked and then pulped or juiced.

Further, the sterilizing temperature is 75-132° C., and the sterilizing time is 2 s to 50 min.

(2) Upon sterilization, cooling the raw materials to 20-45° C., inoculating a probiotic according to a proportion of $10^3$-$10^9$ cfu/mL, and fermenting for 6-96 h at 25-45° C., a pH value of 2.5-5.0 being a fermentation endpoint, The probiotic is a strain of *Lactobacillus casei* NCU215, which was preserved in China General Microbiological Culture Collection Center (CGMCC) (Address: Institute of Microbiology of Chinese Academy of Sciences, No. 3, No. 1 Beichen West Road, Chaoyang District, Beijing) on Oct. 21, 2019 with a preservation number of CGMCC No. 18702.

The *Lactobacillus casei* NCU215 is screened from a traditional fermented pickle in China, and is a probiotic strain with good fermentability to fruit and vegetable and resistance to an environmental pressure in a digestive tract. The strain has the following physiological properties:

① With 2-h treatment in a PBS at a pH of 2.0, the survival rate is 78.98%.

② With 4-h treatment in an environment containing 0.5% of cholate, the survival rate is 84.89%.

③ By digesting for 3 h in a simulated gastric fluid having a pH of 3.0 and then transferring to a simulated intestinal fluid having a pH of 8.0 to digest for 8 h, the vitality is not significantly reduced.

④ The strain has good surface property and capacity of adhering an intestinal epithelial cell: at 24 h, the auto-aggregation rate is 64.32%, the surface hydrophobic rate is 23.15%, and the adhesion rate to a human colon cancer cell Caco-2 is 7.47%.

⑤ The strain has a good antioxidant activity: the DPPH free radical scavenging rate is 11.91%, the hydroxyl free radical scavenging rate is 10.85%, the total antioxidant capacity is equivalent to 95.90 µmol of Trolox, and the total reducing capacity is equivalent to 0.28 mM $FeSO_4$.

⑥ 24-h fermented supernate of the strain has an excellent antibacterial activity to common food-borne pathogenic bacteria, and particularly has the best inhibitory activity to *Listeria monocytogenes* and *Staphylococcus aureus*, with diameters of bacterial inhibition rings respectively being 23.18 mm and 24.42 mm. Additionally, a test on a hemolytic activity of the strain turns out that the strain is not hemolytic; and a test on an antibiotic sensitivity turns out that the strain is sensitive to tetracycline, ampicillin, amoxicillin, cefalotin, erythromycin and penicillin and tolerant to kanamycin, ciprofloxacin, streptomycin and gentamicin.

⑦ Colony morphology: orange-yellow and round; flat with a smooth surface, a tidy edge, strong acid production and 1-3 mm; and gram-positive with a short rod shaped thallus (see FIG. 1).

In combination with physiological-biochemical characteristics and a 16SrRNA sequence, the strain is identified as the *Lactobacillus casei*, with a phylogenetic tree shown in FIG. 2.

Further, the pH value of the fermentation endpoint is determined according to a demand on different flavors.

(3) Standardizing fermented fruit and vegetable puree to obtain the probiotic fermented fruit and vegetable puree product.

Further, the standardization is to standardize sourness and sweetness of the product according to an industry, enterprise or actual demand; and by means of the standardization, a little difference in acidity, sugar degree or sugar-acid ratio in each batch of fermented products is remedied.

Further, the probiotic fermented fruit and vegetable puree finished product may be put into a refrigerator at 0-4° C. for refrigeration, the shelf life of the product at 0-4° C. being 21 days; may also be subjected to ultra-high temperature instantaneous sterilization for 2 s to 10 min at 85-132° C., and canned in a sterile manner, the shelf life of the product at a room temperature being 18 months; and may also be canned, sealed and sterilized for 20-40 min at 75-132° C., the shelf life of the product at the room temperature being 18 months.

In the present invention, the fruit and vegetable are any one or more of fruits and vegetables such as berries (including strawberry, blueberry, mulberry, blackberry, raspberry, cranberry, etc.); melons (including watermelon, honey-dew melon, muskmelon, muskmelon, etc.); stone fruits (including peach, yellow peach, cherry, plum, waxberry, wild jujube, Chinese olive, longan, litchi, etc.); kernel fruits (including apple, pear, persimmon, loquat, etc.); citruses (including tangerine, mandarin orange, cumquat, lemon, grapefruit, shaddock, pomelo, etc.); root vegetables (including radish, carrot, cabbage, sugar beet, ginger, *radix puerariae*, yam, sweet potato, bamboo sprout, etc.); leaf vegetables (spinach, garland *chrysanthemum*, celery, etc.); and fruit vegetables (including water caltrop, gumbo, tomato, *capsicum*, pumpkin, bitter gourd, etc.).

The present invention has the following beneficial effects:

1. A strain NCU215 used by the present invention has excellent fermentability, and a fast acid production speed in fruit and vegetable raw materials, and makes fermentation time shortened obviously as compared with other *Lactobacillus casei*. Taking carrot puree as a fermentation raw material to inoculate the NCU215, the pH decreasing speed is fast, and the acid production capacity is strong; the pH value of the carrot puree is decreased to 3.8 or less after 8 h of fermentation of the strain NCU215 and decreased to 3.03 after 24 h, and the acidity is 4.34‰.

2. The probiotic fermented fruit and vegetable puree produced by the present invention effectively keeps nutritional ingredients in fresh fruit and vegetable, is mellow in taste, sour and sweet in mouthfeel and strong in function, and has no any essence, pigment or preservative, in line with a requirement of people on healthy, nutritional and functional food.

3. The probiotic fermented fruit and vegetable puree provided by the present invention has the following characteristics: (1) the probiotic fermented fruit and vegetable puree is produced by making a full use of an edible portion of fresh fruit and vegetable, so compared with a juicing-concentrating method of the existing fruit and vegetable puree, raw materials are used more effectively, and the generation of a waste material during production is reduced; (2) the probiotic fermented fruit and vegetable puree may generate a natural mellow sour, effectively remove an astringency in fruit and a wild *Artemisia* flavor in vegetable, and neutralize an unpleasant sour in the fruit; (3) with probiotic fermentation, the present invention may improve a content of amino acid in the fruit and vegetable by 20% or more, generate multiple aromatic substances, improve a flavor substance by 30% or more, and effectively improve a taste and a mouthfeel of the product; (4) the probiotic fermented fruit and vegetable puree fully keeps such nutritional ingredients as a vitamin and a dietary fiber in fruit and vegetable raw materials; and (5) the present invention prolongs a shelf life of the product and prevents rot.

DESCRIPTION OF THE EMBODIMENTS

Figure 1:
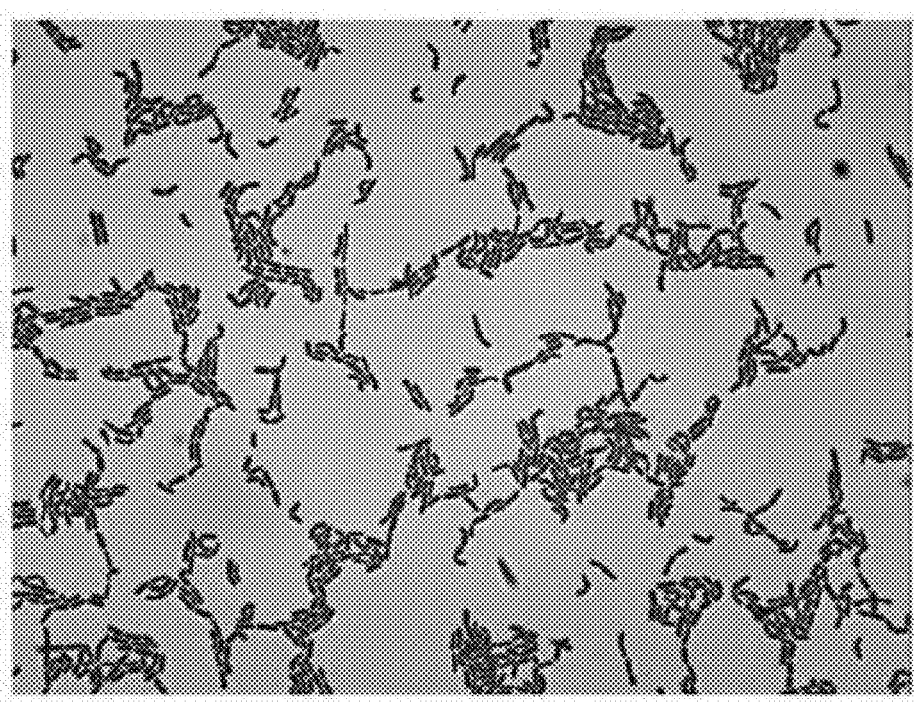
FIG. 1 shows a mycelial morphology of the strain NCU215.
Figure 2:
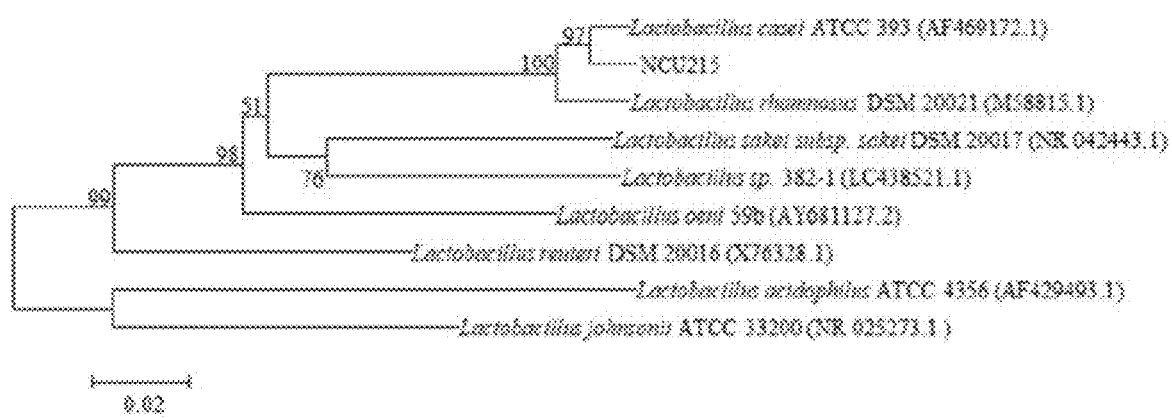
FIG. 2 shows a phylogenetic tree.

In order to make the objectives, technical solutions and advantages of the present invention clearer, the present invention will be further described below in detail in combination with specific embodiments. It should be understood that the specific embodiments described herein are intended to explain the present invention but not limit the present invention.

1. A strain NCU215 used by the present invention has excellent fermentability, and a fast acid production speed in fruit and vegetable raw materials, and makes fermentation time shortened obviously as compared with other *Lactobacillus casei*. Taking carrot puree as a fermentation raw material to inoculate the NCU215, and *Lactobacillus casei* ATCC393 as a fermentation control strain, it is turned out that the strain NCU215 has a fast pH decreasing speed and a strong acid production capacity as compared with the ATCC393 strain. The pH value of the carrot puree is decreased to 3.8 or less after 8 h of fermentation of the strain NCU215 and decreased to 3.03 after 24 h, and the acidity is 4.34‰. However, the pH value of the carrot puree is 4.23 after 8 h of fermentation of the comparative strain and 3.56 after 24 h, and the acidity is only 3.15‰.

2. With the fermentation of the *Lactobacillus casei* NCU215, the fresh and sweet fragrance in the fruit and vegetable puree can be increased, and the bitterness can be reduced. With fermented mango puree and pumpkin puree as examples, compared with *Lactobacillus casei* ATCC393, CICC 6117 and ATCC334, amino acids of a sweet flavor, a fresh flavor and an aromatic flavor in the mango puree and pumpkin puree fermented by the *Lactobacillus casei* NCU215 are significantly improved, whereas an amino acid of a bitter flavor is significantly reduced, with a result shown in table 1 and table 2.

Mango puree fermentation method: a fresh and unrotten mango was selected as a raw material, cleaned, peeled, denucleated and pulped; and puree was stirred uniformly according to components and a proportion (85 parts of mango puree and 15 parts of glucose), and sterilized for 9 min at 102° C. Upon sterilization, a feed liquid was cooled to 37° C.; freeze-dried powder of *Lactobacillus casei* NCU215, ATCC393, CICC 6117 and ATCC334 was respectively inoculated to the sterilized and cooled mango puree according to a proportion of $10^6$ cfu/mL; and fermentation was performed at 37° C., a pH value of 3.0 being a fermentation endpoint.

Pumpkin puree fermentation method: a fresh and unrotten pumpkin was selected as a raw material, precooked and pulped; and puree was stirred uniformly according to components and a proportion (82 parts of pumpkin puree and 18 parts of white granulated sugar), and sterilized for 12 min at 100° C. Upon sterilization, a feed liquid was cooled to 38° C.; freeze-dried powder of *Lactobacillus casei* NCU215, ATCC393, CICC 6117 and ATCC334 was respectively inoculated to the sterilized and cooled pumpkin puree according to a proportion of $10^6$ cfu/mL; and fermentation was performed at 37° C., a pH value of 3.9 being a fermentation endpoint.

TABLE 1

Change of amino acid before and after fermentation of mango puree

| | | | Content (mg/g) | | | |
|---|---|---|---|---|---|---|
| Type of amino acid | Flavor | Before fermentation | After fermentation of NCU215 | After fermentation of ATCC393 | After fermentation of CICC6117 | After fermentation of ATCC334 |
| Threonine | Fresh | 0.38 | 1.32 | 0.69 | 0.75 | 0.87 |
| Aspartic acid | Fresh | 0.14 | 0.16 | 0.12 | 0.14 | 0.11 |
| Serine | Sweet | 0.10 | 0.09 | 0.06 | 0.07 | 0.09 |
| Methionine | Bitter | 0.005 | 0.004 | 0.008 | 0.006 | 0.007 |
| Glutamic acid | Fresh | 0.16 | 0.18 | 0.13 | 0.13 | 0.15 |
| Glycine | Sweet | 0.01 | 0.027 | 0.008 | 0.015 | 0.012 |
| Alanine | Sweet | 0.28 | 0.31 | 0.14 | 0.25 | 0.29 |
| Cysteine | Aromatic | 0.012 | 0.016 | 0.015 | 0.013 | 0.012 |
| Valine | Bitter | 0.03 | 0.01 | 0.03 | 0.02 | 0.02 |
| Histidine | Sweet | 0.033 | 0.035 | 0.025 | 0.031 | 0.033 |
| Lysine | Fresh | 0.01 | 0.086 | 0.021 | 0.035 | 0.026 |
| Proline | Sweet | 0.035 | 0.035 | 0.033 | 0.029 | 0.031 |
| Arginine | Bitter | 0.15 | 0.14 | 0.16 | 0.15 | 0.15 |
| Isoleucine | Bitter | 0.012 | 0 | 0.015 | 0.011 | 0.009 |
| Leucine | Bitter | 0.01 | 0 | 0.012 | 0.011 | 0.007 |
| Tyrosine | Aromatic | 0.015 | 0.022 | 0.017 | 0.016 | 0.019 |
| Phenylalanine | Aromatic | 0.02 | 0.03 | 0 | 0.03 | 0.02 |

TABLE 2

Change of amino acid before and after fermentation of pumpkin puree

| | | | Content (mg/g) | | | |
|---|---|---|---|---|---|---|
| Type of amino acid | Flavor | Before fermentation | NCU215 After fermentation | After fermentation of ATCC393 | After fermentation of CICC6117 | ATCC334 After fermentation |
| Threonine | Fresh | 0.47 | 1.79 | 0.65 | 0.58 | 0.66 |
| Aspartic acid | Fresh | 0.19 | 0.33 | 0.21 | 0.20 | 0.29 |
| Serine | Sweet | 1.24 | 2.84 | 1.57 | 1.98 | 1.75 |
| Glutamic acid | Fresh | 0.45 | 0.99 | 0.44 | 0.48 | 0.86 |
| Glycine | Sweet | 0.02 | 0.04 | 0.02 | 0.03 | 0.02 |

TABLE 2-continued

Change of amino acid before and after fermentation of pumpkin puree

| | | Content (mg/g) | | | | |
|---|---|---|---|---|---|---|
| Type of amino acid | Flavor | Before fermentation | NCU215 After fermentation | After fermentation of ATCC393 | After fermentation of CICC6117 | ATCC334 After fermentation |
| Alanine | Sweet | 0.27 | 0.47 | 0.23 | 0.39 | 0.31 |
| Valine | Bitter | 0.21 | 0.18 | 0.20 | 0.19 | 0.20 |
| Methionine | Bitter | 0.007 | 0.003 | 0.008 | 0.006 | 0.007 |
| Isoleucine | Bitter | 0.08 | 0.07 | 0.07 | 0.06 | 0.08 |
| Leucine | Bitter | 0.09 | 0.05 | 0.07 | 0.08 | 0.07 |
| Cysteine | Aromatic | 0.033 | 0.057 | 0.035 | 0.049 | 0.038 |
| Tyrosine | Aromatic | 0.10 | 0.05 | 0.07 | 0.08 | 0.07 |
| Phenylalanine | Aromatic | 0.02 | 0.13 | 0.12 | 0.09 | 0.08 |
| Histidine | Sweet | 0.17 | 0.19 | 0.16 | 0.17 | 0.18 |
| Lysine | Fresh | 0.07 | 0.14 | 0.09 | 0.08 | 0.10 |
| Arginine | Bitter | 0.19 | 0.13 | 0.19 | 0.18 | 0.17 |

3. Because of the fermentation of the *Lactobacillus casei* NCU215, the antioxidant substance in the fruit and vegetable puree is increased, the antioxidant capacity is enhanced, and the influence on a vitamin is relatively small. With the foregoing mango puree as an example, in the mango puree fermented by the *Lactobacillus casei* NCU215, such important antioxidant substances as polyphenol and flavone are increased, and the antioxidant capacity is enhanced. In the mango puree fermented by the comparative strains ATCC393, CICC 6117 and ATCC334, such important antioxidant substances as polyphenol and flavone and the antioxidant capacity are not increased significantly. For the mango puree fermented by all strains, a total content of vitamin C, beta-carotene and carotenoid is reduced to some extent. Nevertheless, compared with the comparative strains of *Lactobacillus casei* ATCC393, CICC 6117 and ATCC334, the total content of vitamin C, beta-carotene and carotenoid in the mango puree fermented by the *Lactobacillus casei* NCU215 is reduced minimally, with a result shown in table 3 and table 4.

TABLE 3

Content of antioxidant substance before and after fermentation of mango puree

| Antioxidant substance | Before fermentation | After fermentation of NCU215 | After fermentation of ATCC393 | After fermentation of CICC6117 | After fermentation of ATCC334 |
|---|---|---|---|---|---|
| Vitamin C (mg/100 g) | 97.61 | 92.24 | 90.58 | 91.32 | 90.87 |
| Beta-carotene (mg/100 g) | 0.87 | 0.77 | 0.59 | 0.67 | 0.59 |
| Total content of carotenoid (mg/100 g) | 1.53 | 1.15 | 0.89 | 1.03 | 0.99 |
| Polyphenol (mg GAE/100 g) | 88.58 | 97.96 | 87.23 | 89.73 | 88.52 |
| Total flavones (mg DW/100 g) | 71.61 | 75.08 | 70.01 | 70.69 | 71.79 |

TABLE 4

Change of antioxidant capacity of mango puree before and after fermentation

| Determination method | Equivalent weight of antioxidant substance | Before fermentation | After fermentation of NCU215 | After fermentation of ATCC393 | After fermentation of CICC6117 | After fermentation of ATCC334 |
|---|---|---|---|---|---|---|
| FRAP | $FeSO_4$ (mM) | 5.22 | 5.96 | 5.01 | 5.23 | 5.55 |
| ABTS | $V_E$ (mM) | 4.25 | 4.21 | 4.17 | 4.18 | 4.06 |
| DPPH free radical scavenging rate | $V_C$ (mg/100 mL) | 20.39 | 21.86 | 19.73 | 20.56 | 20.74 |
| Hydroxyl free radical scavenging rate | $V_C$ (mg/mL) | 0.44 | 0.54 | 0.42 | 0.51 | 0.49 |

4. Thanks to the fermentation of the *Lactobacillus casei* NCU215, the storage stability is very good. Upon the completion of fermentation same as the foregoing mango puree fermentation method, by performing ultra-high temperature instantaneous sterilization for 3 s at 132° C., and filling in a sterile manner, a content of relevant substance is determinated.

TABLE 5

Change of quality during storage of fermented mango puree

| Storage time/d | pH | acidity g/kg | Soluble solid/% | Sugar content mg/g | Content of organic acid mg/g | Crude protein g/100 g | Vitamin C mg/100 g |
|---|---|---|---|---|---|---|---|
| 0 | 3.41 | 10.16 ± 0.04 | 17.9 ± 0.02 | 95.32 ± 0.15 | 25.46 ± 0.04 | 0.57 ± 0.00 | 83.46 ± 0.25 |
| 30 | 3.42 | 10.19 ± 0.17 | 18 ± 0.10 | 94.68 ± 0.40 | 24.48 ± 0.55 | 0.56 ± 0.01 | 81.58 ± 0.39 |
| 60 | 3.4 | 10.21 ± 0.12 | 18.1 ± 0.04 | 94.32 ± 0.19 | 25.06 ± 0.36 | 0.57 ± 0.01 | 79.78 ± 1.00 |
| 90 | 3.41 | 10.17 ± 0.02 | 17.9 ± 0.12 | 93.38 ± 0.05 | 24.59 ± 0.28 | 0.54 ± 0.02 | 74.33 ± 0.84 |
| 120 | 3.43 | 10.12 ± 0.03 | 18 ± 0.05 | 92.27 ± 0.10 | 24.01 ± 0.07 | 0.54 ± 0.03 | 70 ± 0.45 |
| 150 | 3.43 | 10.12 ± 0.12 | 17.8 ± 0.01 | 93.11 ± 0.02 | 23.81 ± 0.02 | 0.52 ± 0.02 | 66.45 ± 1.24 |
| 180 | 3.44 | 10.09 ± 0.13 | 17.8 ± 0.03 | 92.34 ± 0.50 | 23.21 ± 0.04 | 0.53 ± 0.04 | 62.59 ± 0.69 |

As can be seen from the above table, the contents of sugar and organic acid in the mango puree product fermented by the probiotic NCU215 change a little. At the 6th month, the preserving rates of the sugar and the organic acid are still very high, and are respectively 96.8% and 91.2%. For the content of protein, the preserving rate at the end of storage is up to 93%. The content of vitamin C tends to decline overall; and at the 6th month, it is determinated that the content is reduced by 35% as compared with an initial stage. The vitamin C is oxidized and decomposed easily, but compared with a change trend of the VC of a common mango beverage during storage, the preserving rate for the VC of the fermented mango puree is high.

5. The fermented fruit and vegetable puree provided by the present invention has the following functions compared with a common fruit and vegetable puree product: (1) the puree enhances immunity of a human body and prevents enteritis and intestinal cancer; (2) the puree may regulate blood fat and reduce cholesterol; (3) it moistens and relaxes the bowels; and (4) the probiotic fermented fruit and vegetable puree containing viable bacteria has an important regulation effect to a microecological balance of an intestinal tract of the human body.

6. The 16SrRNA sequence of the strain NCU215 is as follows (sequence table SEQ ID NO. 1):

CGGCAGTGCGGGTGCTATACATGCAAGTCGAACGAGTTCTCGTTGATGAT

CGGTGCTTGCACCGAGATTCAACATGGAACGAGTGGCGGACGGGTGAGTA

ACACGTGGGTAACCTGCCCTTAAGTGGGGGATAACATTTGGAAACAGATG

CTAATACCGCATAGATCCAAGAACCGCATGGTTCTTGGCTGAAAGATGGC

GTAAGCTATCGCTTTTGGATGGACCCGCGGCGTATTAGCTAGTTGGTGAG

GTAATGGCTCACCAAGGCGATGATACGTAGCCGAACTGAGAGGTTGATCG

GCCACATTGGGACTGAGACACGGCCCAAACTCCTACGGGAGGCAGCAGTA

GGGAATCTTCCACAATGGACGCAAGTCTGATGGAGCAACGCCGCGTGAGT

GAAGAAGGCTTTCGGGTCGTAAAACTCTGTTGTTGGAGAAGAATGGTCGG

CAGAGTAACTGTTGCCGGCGTGACGGTATCCAACCAGAAAGCCACGGCTA

ACTACGTGCCAGCAGCCGCGGTAATACGTAGGTGGCAAGCGTTATCCGGA

TTTATTGGGCGTAAAGCGAGCGCAGGCGGTTTTTTAAGTCTGATGTGAAA

GCCCTCGGCTTAACCGAGGAAGCGCATCGGAAACTGGGAAACTTGAGTGC

AGAAGAGGACAGTGGAACTCCATGTGTAGCGGTGAAATGCGTAGATATAT

GGAAGAACACCAGTGGCGAAGGCGGCTGTCTGGTCTGTAACTGACGCTGA

GGCTCGAAAGCATGGGTAGCGAACAGGATTAGATACCCTGGTAGTCCATG

CCGTAAACGATGAATGCTAGGTGTTGGAGGGTTTCCGCCCTTCAGTGCCG

CAGCTAACGCATTAAGCATTCCGCCTGGGGAGTACGACCGCAAAGGTTGA

AACTCAAAGGAATTGACGGGGGCCCGCACAAGCGGTGGAGCATGTGGGTT

TAATTCGAAGCAACGCGAAGAACCCTTACCAGGTCTTGACATCTTTTGAT

CACCTGAGAGATCAGTTTTCCCCTTTCGGGGCAAAATGACAGGTGGTGCA

TGATGTCGTCAGCCTCGTGTCGTGAGATGGTGGGGTAGGTCCCGCACGAG

CGCACCTATGAACTAGTGCAGCATTAGTTGGTCACTCTAGTAGACTGCAG

TGACGACCGGAGGCAACGTTGGAATGAACGGTTCAATTCATCAG.

7. Determination Method (1) A flavor substance is detected as follows:

A static headspace-gas chromatography-mass spectrometry is used, and the flavor substance is detected by using an Agilent triple series quadrupole gas chromatograph-mass spectrometer, with conditions for gas chromatography and mass spectrometry as follows:

Chromatographic column: HP-5 quartz capillary column (30 m*0.25 mm, 1 μm);

Heating process: an initial temperature is 50° C. and is kept for 3 min, then is heated to 120° C. at 2° C./min, and at last is heated to 250° C. at 20° C./min and kept for 5 min; and a carrier gas (He) has a flow velocity of 1.0 mL/min, a pressure of 7.6522 psi, a sample size of 1 μL and no flow diversion.

An electron ionization ion source has electron energy of 70 eV, a mass scanning range of 35-450 m/z and 20 scans/s, and a temperature of 230° C.

The "-" in the flavor substance table denotes that the substance is undetected in the sample.

(2) An amino acid detection method is to determinate a type and content of amino acid in the sample by using an amino acid analyzer according to GB/T 5009.124-2003 Determination of Amino Acids in Foods.

The present invention is further described below in combination with specific embodiments.

Embodiment 1: Probiotic Fermented Pear Puree

For the probiotic fermented pear puree, a proportion of raw materials is as follows: 89.9 parts of pear puree, 10 parts of glucose and 0.1 parts of D-sodium isoascorbiate.

A fresh and unrotten pear was selected as a raw material; sarcocarp was taken and pulped; and puree was stirred uniformly according to the above components and proportion, and sterilized for 2 min at 105° C. Upon sterilization, a feed liquid was cooled to 35° C., freeze-dried powder of *Lactobacillus casei* NCU215 was inoculated to the sterilized and cooled raw material according to a proportion of $10^4$ cfu/mL, and fermentation was performed for 72 h at 35° C., a pH value of 3.8 being a fermentation endpoint. Fermented pear puree was standardized in sweetness and sourness to obtain the probiotic fermented pear puree finished product. The standardized fermented pear puree was subjected to ultra-high temperature instantaneous sterilization for 3 s at 132° C., and filled in a sterile manner, a shelf life of the product at a room temperature being 18 months.

Embodiment 2: Probiotic Fermented Honey-Dew Melon Puree

For the probiotic fermented honey-dew melon puree, a proportion of raw materials is as follows: 89.9 parts of honey-dew melon puree, 10 parts of malt syrup and 0.1 parts of D-sodium isoascorbiate.

A fresh and unrotten honey-dew melon was selected as a raw material, cleaned, peeled, seeded and pulped; and puree was stirred uniformly according to the above components and proportion, and sterilized for 3 min at 100° C. Upon sterilization, a feed liquid was cooled to 40° C., inoculated with freeze-dried powder of *Lactobacillus casei* NCU215 according to a proportion of $10^3$ cfu/mL, and fermented for 90 h at 37° C., a pH value of 2.8 being a fermentation endpoint. Fermented honey-dew melon puree was standardized in sweetness and sourness to obtain the probiotic fermented honey-dew melon puree finished product. The standardized fermented honey-dew melon puree was put into a refrigerator at 0-4° C. for refrigeration, a shelf life of the product at 0-4° C. being 21 days.

Embodiment 3: Probiotic Fermented Peach Puree

For the probiotic fermented peach puree, a proportion of raw materials is as follows: 89.9 parts of peach puree, 10 parts of erythritol and 0.1 parts of D-sodium isoascorbiate.

A fresh and unrotten peach was selected as a raw material, cleaned, denucleated and pulped; and puree was stirred uniformly according to the above components and proportion, and sterilized for 8 min at 90° C. Upon sterilization, a feed liquid was cooled to 37° C., inoculated with freeze-dried powder of *Lactobacillus casei* NCU215 according to a proportion of $10^6$ cfu/mL, and fermented for 72 h at 37° C., a pH value of 3.1 being a fermentation endpoint. Fermented peach puree was standardized in sweetness and sourness to obtain the probiotic fermented peach puree finished product. The standardized fermented peach puree was subjected to ultra-high temperature instantaneous sterilization for 3 s at 132° C., and filled in a sterile manner, a shelf life of the product at a room temperature being 18 months.

Embodiment 4: Probiotic Fermented Bitter Gourd Puree

For the probiotic fermented bitter gourd puree, a proportion of raw materials is as follows: 84.95 parts of bitter gourd puree, 5 parts of erythritol and 0.05 parts of D-sodium isoascorbiate.

A fresh and unrotten bitter gourd was selected as a raw material, cleaned, seeded and pulped; and puree was stirred uniformly according to the above components and proportion, and sterilized for 2 s at 132° C. Upon sterilization, a feed liquid was cooled to 30° C., inoculated with freeze-dried powder of *Lactobacillus casei* NCU215 according to a proportion of $10^4$ cfu/mL, and fermented for 82 h at 32° C., a pH value of 3.0 being a fermentation endpoint. Fermented bitter gourd puree was standardized in sweetness and sourness to obtain the probiotic fermented bitter gourd puree finished product. The standardized fermented bitter gourd puree was put into a refrigerator at 0-4° C. for refrigeration, a shelf life of the product at 0-4° C. being 21 days.

Embodiment 5: Probiotic Fermented Celery Puree

For the probiotic fermented celery puree, a proportion of raw materials is as follows: 80.95 parts of celery puree, 19 parts of erythritol and 0.05 parts of D-sodium isoascorbiate.

A fresh and unrotten celery was selected as a raw material, cleaned and pulped; and puree was stirred uniformly according to the above components and proportion, and sterilized for 1 min at 112° C. Upon sterilization, a feed liquid was cooled to 42° C., inoculated with freeze-dried powder of *Lactobacillus casei* NCU215 according to a proportion of $10^5$ cfu/mL, and fermented for 54 h at 38° C., a pH value of 2.8 being a fermentation endpoint. Fermented celery puree was standardized in sweetness and sourness to obtain the probiotic fermented celery puree finished product. The standardized fermented celery puree was canned, sealed and sterilized for 30 min at 115° C., a shelf life of the product at a room temperature being 18 months.

Embodiment 6: Probiotic Fermented Blueberry Puree

For the probiotic fermented blueberry puree, a proportion of raw materials is as follows: 82.1 parts of blueberry puree, 17.8 parts of glucose and 0.1 parts of D-sodium isoascorbiate.

A fresh and unrotten blueberry was selected as a raw material, cleaned and pulped; and puree was stirred uniformly according to the above components and proportion, and sterilized for 10 min at 85° C. Upon sterilization, a feed liquid was cooled to 35° C., inoculated with freeze-dried powder of *Lactobacillus casei* NCU215 according to a proportion of $10^9$ cfu/mL, and fermented for 72 h at 35° C., a pH value of 2.5 being a fermentation endpoint. Fermented blueberry puree was standardized in sweetness and sourness to obtain the probiotic fermented blueberry puree finished product. The standardized fermented blueberry puree was put into a refrigerator at 0-4° C. for refrigeration, a shelf life of the product at 0-4° C. being 21 days.

Embodiment 7: Probiotic Fermented Tomato Puree

For the probiotic fermented tomato puree, a proportion of raw materials is as follows: 85.3 parts of tomato puree, 14.6 parts of maltitol and 0.1 parts of D-sodium isoascorbiate.

A fresh and unrotten tomato was selected as a raw material, cleaned and pulped; and after peel was filtered, puree was stirred uniformly according to the above components and proportion, and sterilized for 2 min at 105° C. Upon sterilization, a feed liquid was cooled to 37° C., inoculated with freeze-dried powder of *Lactobacillus casei* NCU215 according to a proportion of $10^5$ cfu/mL, and fermented for 72 h at 38° C., a pH value of 2.8 being a fermentation endpoint. Fermented tomato puree was standardized in sweetness and sourness to obtain the probiotic fermented tomato puree finished product. The standardized fermented tomato puree was subjected to ultra-high temperature instantaneous sterilization for 3 s at 132° C., and filled in a sterile manner, a shelf life of the product at a room temperature being 18 months.

Embodiment 8: Probiotic Fermented Ginger Puree

For the probiotic fermented ginger puree, a proportion of raw materials is as follows: 84.07 parts of ginger puree, 15.9 parts of starch syrup and 0.03 parts of D-sodium isoascorbiate.

A fresh and unrotten ginger was selected as a raw material, cleaned, peeled and pulped; and puree was stirred uniformly according to the above components and proportion, and sterilized for 10 min at 85° C. Upon sterilization, a feed liquid was cooled to 38° C., inoculated with freeze-dried powder of *Lactobacillus casei* NCU215 according to a proportion of $10^7$ cfu/mL, and fermented for 96 h at 32° C., a pH value of 2.7 being a fermentation endpoint. Fermented ginger puree was standardized in sweetness and sourness to obtain the probiotic fermented ginger puree finished product. The standardized fermented ginger puree was subjected to ultra-high temperature instantaneous sterilization for 3 s at 132° C., and filled in a sterile manner, a shelf life of the product at a room temperature being 18 months.

Embodiment 9: Probiotic Fermented Sweet Potato Puree

For the probiotic fermented sweet potato puree, a proportion of raw materials is as follows: 85.09 parts of sweet potato puree, 14.9 parts of malt syrup and 0.01 parts of D-sodium isoascorbiate.

A fresh and unrotten sweet potato was selected as a raw material, precooked, peeled and pulped; and puree was stirred uniformly according to the above components and proportion, and sterilized for 3 min at 101° C. Upon sterilization, a feed liquid was cooled to 40° C., inoculated with freeze-dried powder of *Lactobacillus casei* NCU215 according to a proportion of $10^4$ cfu/mL, and fermented for 50 h at 37° C., a pH value of 2.6 being a fermentation endpoint. Fermented sweet potato puree was standardized in sweetness and sourness to obtain the probiotic fermented sweet potato puree finished product. The standardized fermented sweet potato puree was canned, sealed and sterilized for 30 min at 115° C., a shelf life of the product at a room temperature being 18 months.

Embodiment 10: Probiotic Fermented Banana Puree

For the probiotic fermented banana puree, a proportion of raw materials is as follows: 87.99 parts of banana puree, 12 parts of starch syrup and 0.01 parts of D-sodium isoascorbiate.

A fresh and unrotten banana was selected as a raw material, peeled and pulped; and puree was stirred uniformly according to the above components and proportion, and sterilize for 10 min at 85° C. Upon sterilization, a feed liquid was cooled to 40° C., inoculated with freeze-dried powder of *Lactobacillus casei* NCU215 according to a proportion of $10^7$ cfu/mL, and fermented for 60 h at 34° C., a pH value of 3.0 being a fermentation endpoint. Fermented banana puree was standardized in sweetness and sourness to obtain the probiotic fermented banana puree finished product. The standardized fermented banana puree was canned, sealed and sterilized for 30 min at 115° C., a shelf life of the product at a room temperature being 18 months.

Embodiment 11: Probiotic Fermented Pineapple Puree

For the probiotic fermented pineapple puree, a proportion of raw materials is as follows: 84.95 parts of pineapple puree, 5 parts of isomaltooligosaccharide and 0.05 parts of D-sodium isoascorbiate.

A fresh and unrotten pineapple was selected as a raw material, peeled and pulped; and puree was stirred uniformly according to the above components and proportion, and sterilized for 2 s at 132° C. Upon sterilization, a feed liquid was cooled to 32° C., inoculated with freeze-dried powder of *Lactobacillus casei* NCU215 according to a proportion of $10^5$ cfu/mL, and fermented for 48 h at 32° C., a pH value of 2.8 being a fermentation endpoint. Fermented pineapple puree was standardized in sweetness and sourness to obtain the probiotic fermented pineapple puree finished product. The standardized fermented pineapple puree was put into a refrigerator at 0-4° C. for refrigeration, a shelf life of the product at 0-4° C. being 21 days.

Embodiment 12: Probiotic Fermented Wolfberry Puree

For the probiotic fermented wolfberry puree, a proportion of raw materials is as follows: 81.97 parts of wolfberry puree, 18 parts of erythritol and 0.03 parts of D-sodium isoascorbiate.

A fresh and unrotten wolfberry was selected as a raw material, cleaned and pulped; and puree was stirred uniformly according to the above components and proportion, and sterilized for 1 min at 112° C. Upon sterilization, a feed liquid was cooled to 37° C., inoculated with freeze-dried powder of *Lactobacillus casei* NCU215 according to a proportion of $10^6$ cfu/mL, and fermented for 46 h at 37° C., a pH value of 2.7 being a fermentation endpoint. Fermented wolfberry puree was standardized in sweetness and sourness to obtain the probiotic fermented wolfberry puree finished product. The standardized fermented wolfberry puree was canned, sealed and sterilized for 30 min at 115° C., a shelf life of the product at a room temperature being 18 months.

Embodiment 13 Standard on Evaluation of Shelf Life

The shelf life of the present invention is determined by means of the following indicators:

Change in sensory quality and number of bacteria during storage of unsterilized fermented fruit and vegetable puree at 0-4° C.

| | Sensory quality | | | | Number of bacteria | |
|---|---|---|---|---|---|---|
| Retention time/days | Color | Odor | Taste | Tissue state | Total bacterial count | Coliform |
| 0 | Unchanged | Unchanged | Unchanged | Unchanged | ≥10⁹ cfu/mL | Undetected |
| 7 | Unchanged | Unchanged | Unchanged | Unchanged | ≥10⁹ cfu/mL | Undetected |
| 14 | Unchanged | Unchanged | Unchanged | Unchanged | ≥10⁹ cfu/mL | Undetected |
| 21 | Unchanged | Unchanged | Unchanged | Unchanged | ≥10⁹ cfu/mL | Undetected |
| 28 | Unchanged | Unchanged | Souring | Unchanged | ≥10⁹ cfu/mL | >1 cfu/mL |

Change in sensory quality and number of bacteria during storage of sterilized fermented puree at room temperature

| | Sensory quality | | | | Number of bacteria | |
|---|---|---|---|---|---|---|
| Retention time/months | Color | Odor | Taste | Tissue state | Total bacterial count | Coliform |
| 0 | Unchanged | Unchanged | Unchanged | Unchanged | 0 | Undetected |
| 6 | Unchanged | Unchanged | Unchanged | Unchanged | 0 | Undetected |
| 12 | Unchanged | Unchanged | Unchanged | Unchanged | 0 | Undetected |
| 18 | Unchanged | Unchanged | Unchanged | Unchanged | 0 | Undetected |
| 20 | Unchanged | Unchanged | Unchanged | Unchanged | >100 cfu/mL | >1 cfu/mL |

Embodiment 15 Determination of Physiological-Biochemical Characteristics of NCU215

① Test on Acid Resistance—with 2-h Treatment in a PBS at a pH of 2.0, the Survival Rate is 78.98%.

A selected NCU215 was activated twice by using an MRS liquid culture medium, and cultured for 24 h at 37° C. according to 2% (v/v) of inoculum size; and 10000 g was centrifuged for 5 min to collect a thallus. The thallus was re-suspended with a sterile PBS having a pH of 2.0, the concentration of viable bacteria was regulated to $10^8$ CFU/m, incubation was performed for 2 h at 37° C., and a dilution spread method was used to determinate the number of viable bacteria before and after the incubation, thus determining the survival rate. The survival rate was calculated as per the following formula.

$$\text{Survival rate } (\%) = \frac{\log N_1}{\log N_0} \times 100$$

Where, the $N_1$ is the number of survival viable bacteria after the incubation and the $N_0$ is the initial number of bacteria.

② Test on Cholate Resistance—with 4-h Treatment in an Environment Containing 0.5% of Cholate, the Survival Rate is 84.89%.

10000 g of NCU215 that was cultured for 24 h was centrifuged for 5 min at 4° C. to collect a thallus; the obtained thallus was re-suspended with a sterile PBS containing 0.5% of cholate, the concentration of viable bacteria was regulated to $10^8$ CFU/m, incubation was performed for 4 h at 37° C., and a dilution spread method was used to determinate the number of viable bacteria to evaluate the cholate resistance of the NCU215. The survival rate of the NCU215 was calculated according to the following formula.

$$\text{Survival rate } (\%) = \frac{\log N_1}{\log N_0} \times 100$$

Where, the $N_1$ is the number of survival viable bacteria and the $N_0$ is the initial number of bacteria.

③ Tolerance in Simulated Gastric and Intestinal Fluid 10000 g of NCU215 that was cultured for 24 h was centrifuged for 5 min at 4° C. to collect a thallus, and the thallus was cleaned twice with a sterile PBS; thereafter, the thallus was re-suspended in a simulated gastric fluid having a pH of 3.0 to incubate for 3 h at 37° C., and the number of viable bacteria was determinated at 0 h, 1 h, 2 h, and 3 h; and then, 1 mL of culture was added to 9 mL of simulated intestinal fluid to incubate for 8 h at 37° C., and the number of viable bacteria in the culture was determinated at 0 h, 2 h, 4 h and 8 h. The survival rate of the NCU215 was calculated according to the following formula.

$$\text{Survival rate } (\%) = \frac{\log N_1}{\log N_0} \times 100$$

Where, the $N_1$ is the number of survival viable bacteria and the $N_0$ is the initial number of bacteria.

It is turned out that by digesting for 3 h in a simulated gastric fluid having a pH of 3.0 and then transferring to a simulated intestinal fluid having a pH of 8.0 to digest for 8 h, the vitality is not significantly reduced; with 3-h treatment in the simulated gastric fluid, the survival rate is 101.52±1.67%; and with 8-h treatment in the simulated intestinal fluid, the survival rate is 100.27±2.05%.

④-1 Test on Auto-Aggregation Capacity 10000 g of *Lactobacillus* cultured for overnight was centrifuged for 5 min to collect a thallus, and the thallus was cleaned twice with a sterile PBS buffer solution. Thereafter, the obtained thallus cell was re-suspended with a sterile PBS, regulated to $A_{600}$=0.6±0.05 ($A_0$), and incubated for 24 h at 37° C. after 10 s of vortex oscillation. An upper layer of bacterial suspension was taken at 0 h, 2 h, 4 h, 6 h, 12 h and 24 h, and the absorbancy ($A_t$) was determined at 600 nm, three parallels were determinated at each time, and the test was repeated for three times. The auto-aggregation capacity of the bacteria was calculated according to the following formula.

$$\text{Percentage of auto-aggregation of bacteria} = \left(1 - \frac{A_t}{A_0}\right) \times 100\%$$

Where, the $A_0$ denotes an initial absorbance of the thallus, and the $A_t$ denotes an absorbance of the upper layer of bacterial solution at a t moment.

It is turned out that the auto-aggregation rate of the strain within 24 h is 64.32%.

④-2 Test on Surface Hydrophobicity

A Bacteria Adhesion To Hydrocarbons (BATH) method was used to determinate the surface hydrophobicity of *Lactobacillus*. First of all, 10000 g of *Lactobacillus* cultured for overnight was centrifuged for 5 min to collect a thallus cell, and the thallus cell was cleaned twice with a sterile PBS buffer solution; thereafter, the obtained thallus cell was re-suspended with 0.1 mol/L $KNO_3$ and regulated to $A_{600}$=0.6±0.05 ($A_0$). Then, 1 mL of xylene was taken, and added to 3 mL of thallus cell suspension having a well regulated concentration; and after mixing, the mixed solution was pre-incubated for 10 min at a room temperature, subjected to vortex oscillation for 2 min, and then incubated for 30 min at the room temperature for layering; an aqueous phase was absorbed carefully; and with a sterile PBS as a blank, an OD600 value (A) was determined. The hydrophobicity of the bacteria was calculated according to the following formula.

$$\text{Hydrophobic rate} (\%) = \left(1 - \frac{A_0}{A}\right) \times 100\%$$

Where, the $A_0$ denotes an initial absorbance of the thallus, and the A is an absorbance for a lower layer of aqueous phase after treatment of xylene. It is turned out that the surface hydrophobic rate of the strain is 23.15%.

④-3 Test on Adhesion

A cultured Caco-2 cell was digested with a pancreatin-EDTA digestive fluid, then a cell concentration was regulated to 1.0*$10^5$ pcs/mL with a DMEM complete culture solution, the solution was put into a 6-pore tissue culture plate, 2 mL for each pore, and incubated at 37° C. in a $CO_2$ incubator (5% of $CO_2$ and 95% of air) till the cell was grown to a differentiated single layer, and the solution was changed once every 2 days. The DMEM culture solution in each pore of the tissue culture plate was removed, the culture plate was cleaned twice with a sterile PBS buffer solution, 1 mL of *Lactobacillus* suspension ($10^8$ CFU/mL, OD=1) (Caco-2 cell: number of bacteria≥1:100) re-suspended by a DMEM incomplete culture solution was added, and incubation was performed for 2 h at 37° C. Upon the completion of the incubation, a mixed solution in each pore of the tissue culture plate was removed, and the sterile PBS buffer solution was used for cleaning for 5 times to remove an unadhered thallus cell. 0.5 mL of 0.25% pancreatin was added to incubate for 5 min at 37° C. to digest the cell, and then a cell digestive fluid was subjected to gradient dilution and spread on an MRS solid plate to calculate the number of adhered bacteria. The adhesion was calculated by using the following formula.

$$\text{Adhesion rate} (\%) = N_t/N_0 \times 100$$

Where, the $N_t$ denotes the number of bacteria adhered on the Caco-2 cell, and the No denotes the number of total bacteria in the added NCU215. It is turned out that the adhesion rate of the strain to a human colon cancer cell Caco-2 is 7.47%.

⑤ Test on Antioxidant Activity (the NCU215 Sample Solution has a Thallus Concentration of $10^9$ CFU/mL)

DPPH Free Radical Scavenging Capacity 1.0 mL of NCU215 sample solution was added to 1 mL of ethanol DPPH free radical solution (0.1 mM), mixed uniformly and incubated for 30 min in a dark environment at a room temperature. After 8000 g was centrifuged for 10 min, with PBS and DPPH solutions as controls and an ethanol solution and an NCU215 sample as blanks, the absorbancy of the obtained solution was determined at 517 nm. The scavenging capacity was represented by the following formula.

$$\text{Scavenging rate} (\%) = \left(1 - \frac{A_s - A_b}{A_c}\right) \times 100\%$$

Where, the $A_s$ is the absorbancy of the sample at 517 nm, the $A_b$ is the absorbancy of the blank at 517 nm, and the $A_c$ is the absorbancy of the control at 517 nm.

Hydroxyl Free Radical Scavenging Capacity 1 mL of 2.5 mM phenanthroline, 1 mL of PBS (having a pH of 7.4), 1 mL of 2.5 mM $FeSO_4$ and 1 mL of NCU215 sample were mixed simply. By means of adding 1 mL of 20 mM $H_2O_2$ and incubating for 90 min at 37° C., a reaction started. The absorbancy of a mixture was determined at 536 nm, and a hydroxyl free radical scavenging activity was calculated according to the following formula.

$$\text{Scavenging activity} (\%) = \frac{(A_{sample} - A_{blank})}{(A_{control} - A_{blank})} \times 100\%$$

Where, the $A_{sample}$ is the absorbancy in the presence of the sample and the $H_2O_2$, the $A_{control}$ is the absorbancy in the absence of the sample and the $H_2O_2$, and the $A_{blank}$ is the absorbancy of the control in the absence of the sample and the $H_2O_2$.

ABTS Free Radical Scavenging Capacity

An ABTS working mother solution was prepared according to a specification of an ABTS free radical detection kit (Beyotime), and placed for 16 h away from light at a room temperature; and then, a PBS was used to regulate the absorbance $A_{734}$=0.7±0.01 (ABTS working solution). 200 μL of ABTS working solution was added to each detection pore of a 96-pore plate. 10 μL of PBS was added to a blank control pore; 10 μL of Trolox standard solution having 0.15 mM, 0.3 mM, 0.6 mM, 0.9 mM, 1.2 mM and 1.5 mM was respectively added to a standard curve detection pore; and 10 μL of NCU215 sample was added to a sample detection pore and mixed uniformly and slightly. Upon 6 min of incubation away from the light at the room temperature, $A_{734}$ was determined. The total antioxidant capacity of the sample was calculated according to a standard curve.

Total Reducing Capacity

An FRAP working solution was prepared according to a specification of an FRAP total reducing capacity detection kit (Beyotime). A solution having 0.15 mM, 0.3 mM, 0.6 mM, 0.9 mM, 1.2 mM and 1.5 mM was prepared newly. 180 µL of FRAP working solution was added to each detection pore of a 96-pore plate; 5 µL of PBS solution was added to a blank control pore; 5 µL of newly prepared $FeSO_4$ standard solution having 0.15 mM, 0.3 mM, 0.6 mM, 0.9 mM, 1.2 mM and 1.5 mM was added to a standard curve detection pore; and 5 µL of NCU215 sample was added to a sample detection pore, and mixed uniformly and slightly. Upon 5 min of incubation at 37° C., $A_{593}$ was determinated. The total antioxidant capacity of the sample was calculated according to a standard curve.

It is turned out that the strain has a good antioxidant activity: the DPPH free radical scavenging rate is 11.91%, the hydroxyl free radical scavenging rate is 10.85%, the total antioxidant capacity is equivalent to 95.90 µmol of Trolox, and the total reducing capacity is equivalent to 0.28 mM $FeSO_4$.

⑥-1 Test on Antibacterial Activity

NCU215 was cultured for 24 h at 37° C. in an MRS culture medium, and 10000 g of NCU215 was centrifuged for 10 min at 4° C. A fermentation supernate was filtered by a 0.22 µm filter membrane to remove bacteria to obtain a Cell-Free Supernate (CFS) and the CFS was stored at −80° C. for later use. An antibacterial activity of the NCU215 CFS to pathogenic bacteria was determinated in a punching method, that was, 200 µL of NCU215 CFS was taken, added to an LB plate pore coated by *Escherichia coli, salmonella, Listeria monocytogenes, Pseudomonas aeruginosa, Enterobacter sakazakii, Bacillus cereus* and *Staphylococcus aureus*, and incubated for 12 h at 37° C. to determinate a diameter of a bacterial inhibition ring.

⑥-2 Test on Hemolytic Activity

A single colony of a test strain was selected, scratched to a Columbia blood agar plate, and cultured for 48 h at 37° C. to determine a hemolytic activity. With *Lactobacillus fermenti* CECT5716 as a positive control and *Staphylococcus aureus* as a negative control, the test was repeated for three times.

⑥-3 Test on Antibiotic Sensitivity

K-B (drug sensitive disc agar diffusion test) was used to perform a drug sensitive test, thus evaluating antibiotic resistance of the strain. A thallus concentration of a *Lactobacillus* fermentation broth that was cultured for overnight was regulated to $10^8$ CFU/mL, and 100 µL was absorbed and spread on an MRS plate. Drug sensitive discs of streptomycin (10 mg/mL), ampicillin (10 mg/mL), erythromycin (15 mg/mL), tetracycline (30 mg/mL), gentamicin (gentamicin), kanamycin (30 mg/mL), penicillin (10 mg/mL), cefalotin (15 mg/mL), ciprofloxacin (5 mg/mL) and amoxicillin (30 mg/mL) were respectively and slightly placed on the MRS plate coated by a *Lactobacillus* bacterial solution, and cultured for 24 h at 37° C.; and a vernier caliper was used to determinate a diameter of a bacterial inhibition ring, thus determining the sensitivity of the *Lactobacillus* to the above antibiotics.

It is turned out that a 24-h fermented supernate of the strain has an excellent antibacterial activity to common food-borne pathogenic bacteria, and particularly has the best inhibitory activity to *Listeria monocytogenes* and *Staphylococcus aureus*, with diameters of bacterial inhibition rings respectively being 23.18 mm and 24.42 mm. Additionally, a test on a hemolytic activity of the strain turns out that the strain is not hemolytic; and a test on an antibiotic sensitivity turns out that the strain is sensitive to tetracycline, ampicillin, amoxicillin, cefalotin, erythromycin and penicillin and tolerant to kanamycin, ciprofloxacin, streptomycin and gentamicin.

The above embodiments only describe several implementation manners of the present invention. The description is specific and detailed, but cannot be understood as a limit to a scope of the present invention accordingly. It should be pointed out that the person of ordinary skill in the art may further make multiple changes, combinations and improvement to the above implementation manners without departing from a concept of the present invention and those also belong to the protection scope of the present invention. Therefore, the protection scope of the present invention shall be subjected to the claims.

What is claimed is:

1. A probiotic fermented mango puree, produced by a method comprising:

mixing 85 mass parts of a mango puree and 15 mass parts of glucose to form a starting mixture;

sterilizing the starting mixture to form a pre-fermentation mixture;

adding freeze-dried powder of *L. casei* NCU215 to the pre-fermentation mixture at a final concentration of $10^6$ cfu/ml to form a fermentation mixture;

fermenting the fermentation mixture at 37° C. until a pH value of 3.0 is reached;

then terminating fermentation to produce the fermented mango puree;

wherein the probiotic is *Lactobacillus casei* NCU215 has a preservation number of CGMCC No. 18702 and a 16SrRNA sequence of SEQ ID NO:1; and wherein the fermented mango puree, comprises:

a threonine content of 1.32 mg/ml, a glycine content of 0.027 mg/ml, a lysine content of 0.086 mg/ml, a vitamin C content of 92.24 mg/100 g, a Beta-carotene content of 0.77 mg/100 g, a total carotenoid content of 1.15 mg/100 g, a polyphenol content of 97.96 mg GAE/100 g, and a total flavones content of 75.08 mg DW/100 g; and wherein the fermented mango puree has increased antioxidant substances compared to an unfermented mango puree.

* * * * *